United States Patent
Phelps et al.

(10) Patent No.: US 9,089,790 B2
(45) Date of Patent: *Jul. 28, 2015

(54) HYDROCARBON AND DIVALENT CATION REMOVAL FROM RICH MONO ETHYLENE GLYCOL (MEG) FEED STREAMS BY REGENERABLE FILTERS

(75) Inventors: Daniel W. Phelps, League City, TX (US); Luis Eduardo Caires Fernandez, Cypress, TX (US)

(73) Assignee: Cameron International Corporation, Houston, TX (US)

(*) Notice: Subject to any disclaimer, the term of this patent is extended or adjusted under 35 U.S.C. 154(b) by 319 days.

This patent is subject to a terminal disclaimer.

(21) Appl. No.: 13/593,760

(22) Filed: Aug. 24, 2012

(65) Prior Publication Data

US 2014/0058140 A1    Feb. 27, 2014

(51) Int. Cl.
| | |
|---|---|
| C07C 27/26 | (2006.01) |
| B01D 15/00 | (2006.01) |
| B01D 15/36 | (2006.01) |
| C07C 29/76 | (2006.01) |

(52) U.S. Cl.
CPC .............. *B01D 15/00* (2013.01); *B01D 15/362* (2013.01); *C07C 29/76* (2013.01)

(58) Field of Classification Search
None
See application file for complete search history.

(56) References Cited

U.S. PATENT DOCUMENTS

| | | | |
|---|---|---|---|
| 3,732,320 A | 5/1973 | Ford | |
| 4,518,396 A * | 5/1985 | Rawson | 48/127.3 |
| 5,922,198 A | 7/1999 | Kelly et al. | |
| 6,242,655 B1 | 6/2001 | Husain | |
| 6,425,942 B1 * | 7/2002 | Forster | 95/174 |
| 6,444,095 B1 * | 9/2002 | Evans et al. | 202/174 |
| 8,808,546 B2 * | 8/2014 | Phelps et al. | 210/664 |

FOREIGN PATENT DOCUMENTS

| | | |
|---|---|---|
| CN | 20101115718 | 7/2010 |
| GB | 1219018 | 1/1971 |
| WO | WO9511876 | 5/1995 |

* cited by examiner

*Primary Examiner* — Sudhakar Katakam
(74) *Attorney, Agent, or Firm* — Gable Gotwals

(57) ABSTRACT

A system and process for removing hydrocarbons and divalent cations from a rich MEG feed stream is presented. A hydrocarbon removal bed containing a solid adsorbent material adsorbs the hydrocarbons in the rich MEG feed stream as it passes through the hydrocarbon removal bed. After the hydrocarbons have been removed, the rich MEG feed stream flows through an ion exchange bed containing an ion exchange resin in order to remove divalent cations. The rich MEG feed stream then flows through a flash separator and a distillation column to reclaim MEG. Spent solid adsorbent material in the hydrocarbon removal beds and spent ion exchange resin in the ion exchange beds may be regenerated in place using by-products of the MEG reclamation process.

7 Claims, 1 Drawing Sheet

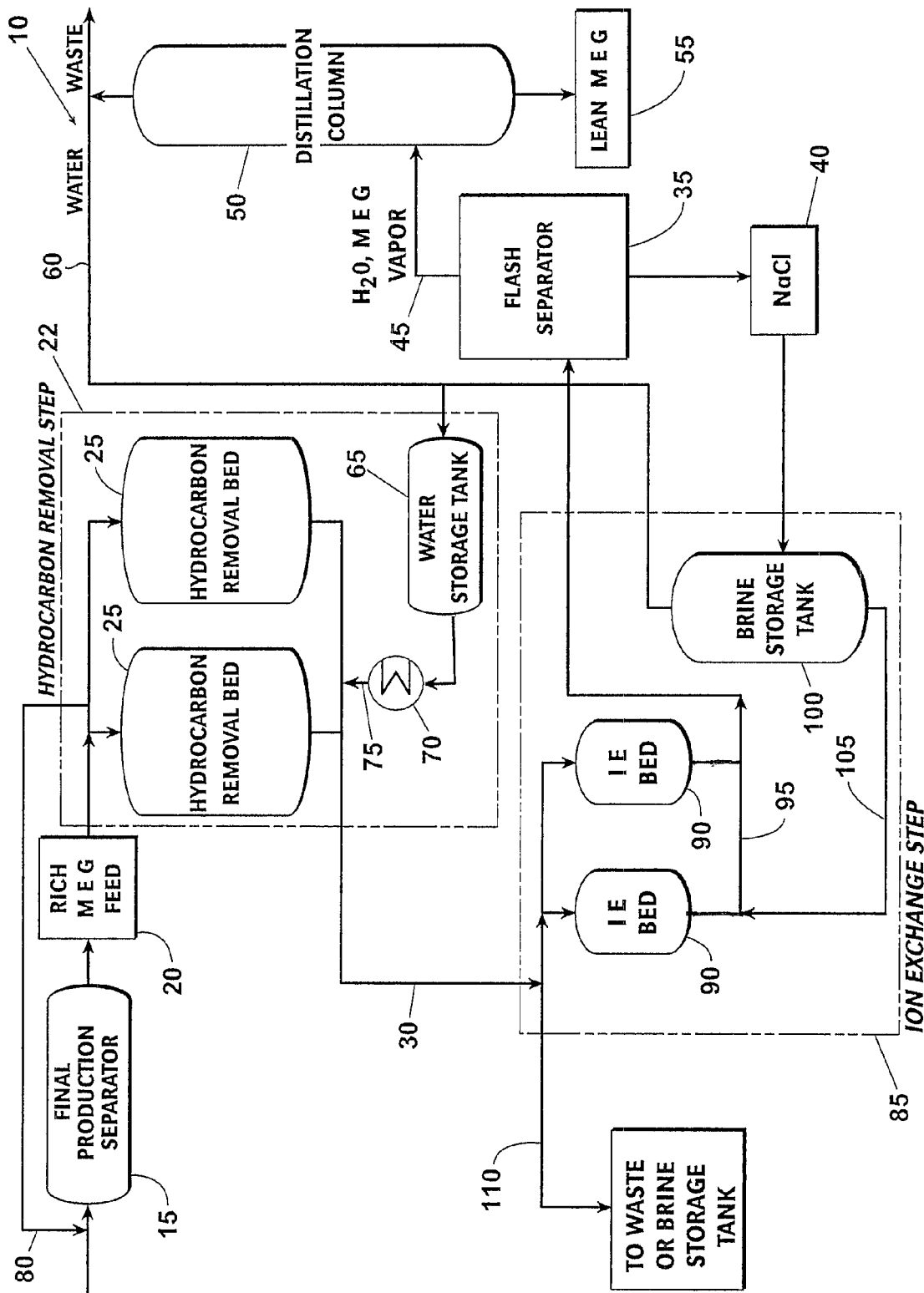

HYDROCARBON AND DIVALENT CATION REMOVAL FROM RICH MONO ETHYLENE GLYCOL (MEG) FEED STREAMS BY REGENERABLE FILTERS

BACKGROUND

Monoethylene glycol (MEG) is commonly used in the oil and gas industry to prevent the formation of gas hydrates in pipelines. The MEG is injected at the wellhead and readily mixes with the produced water to form a mixture referred to as rich MEG.

The oil and rich MEG are separated in the final production separator. However, depending upon the properties of the oil, the hydrocarbon content of the rich MEG may be as high as 1,000 parts per million (ppm). When the oil properties are in the range of a light condensate, the hydrocarbon content may range from 100 ppm to 200 ppm, but even these concentrations may be excessive for optimal operation of the MEG reclamation process.

Increasing the removal of hydrocarbons from the rich MEG will improve the operation of the MEG reclamation process. In addition, hydrocarbon removal eliminates or significantly reduces potential difficulties during the reclamation process. As an example, the rich MEG feed stream must be heated in a heat exchanger before it enters the flash separator. However, the heating process may convert some of the hydrocarbons to a black solid charcoal coke-like material that remains in suspension inside the flash separator. As more of this material forms, it increases the rich MEG's tendency to form a stable foam, reduces the settling of salt crystals, increases the abrasive nature of the rich MEG so that pump seal failure and pipe erosion are more prevalent, and discolors the salt produced in the reclamation process making it unsuitable for marine discharge. In offshore operations, excessive hydrocarbon levels in the rich MEG feed stream can also cause plugging of the downstream lean MEG injection nozzles if the hydrocarbons form a solid compound under line or injection conditions. As another example, hydrocarbons carried with the rich MEG feed stream into the distillation column of the MEG reclamation process must either exit with the distilled water or with the lean MEG. In either case, the hydrocarbons may need to be removed to meet water discharge or product purity specifications. As a final example, hydrocarbons in the rich MEG feed stream may coat the ion exchange resin, reducing the efficiency of any process to remove divalent cations.

Hydrocarbon removal beyond the final production separator is currently limited. Activated charcoal filters are generally used for such removal and are capable of reducing the hydrocarbon levels to the range of approximately 25 to 50 ppm. However, because activated charcoal filters are not very efficient, they are heavy and require large amounts of space and volume. This additional space and weight is very expensive, particularly for offshore operations. In addition, the charcoal filter material must be replaced whenever it is fully adsorbed with hydrocarbons. The spent material may be disposed of as waste or regenerated onshore. Periodically replacing the filter material and properly handling the spent material further increase the costs associated with activated charcoal filters.

In addition to hydrocarbons, the rich MEG feed stream may be loaded with dissolved salt ions from the produced water. Although sodium chloride is commonly the most concentrated salt in the produced water, the feed stream may also contain dissolved divalent salts of magnesium, calcium, strontium, and barium. If these ions are not removed before the MEG and water are separated, they will precipitate and accumulate in the process equipment, eventually leading to failure of the reclamation process.

In the current process for separating divalent cations from the rich MEG feed stream, the cations react with additional carbonate or hydroxide to form insoluble salt crystals, which are then removed from the feed stream. This process generally requires the addition of caustic and acid to completely remove the divalent cations and to neutralize the feed stream before it enters the MEG reclamation process.

The time and temperature of the current separation process must be strictly controlled. In addition, the process requires large and expensive equipment, as well as additional chemicals that are not inherently available as part of the MEG reclamation process. These chemicals must be obtained from outside sources which can be very expensive, particularly when delivered to offshore platforms in remote parts of the world. The chemicals may also be a safety concern, require specialized handling and storage, and increase training, reporting, and recordkeeping requirements. The current separation process also produces a carbonate salt in the form of a solid or slurry material that is generally insoluble and requires disposal as a waste. Proper disposal of this material can be expensive, time-consuming, and labor-intensive. Disposal is even more difficult in offshore applications where temporary storage space and transportation to an approved disposal site are not readily available.

A need exists for systems and processes to remove hydrocarbons and divalent cations from rich MEG feed streams in order to improve the efficiency and eliminate problems during the MEG reclamation process. A need also exists for systems and processes that are less expensive, easier to operate, do not require large amounts of space or additional chemicals, can be regenerated without removing and processing the adsorbent material, and facilitate the disposal of process waste streams.

SUMMARY OF THE INVENTION

A system for removing hydrocarbons and divalent cations from a rich MEG feed stream is presented. The system includes a hydrocarbon removal bed containing a solid adsorbent material that adsorbs the hydrocarbons in the process stream as it flows through the hydrocarbon removal bed. After the hydrocarbons have been removed, the process stream flows through an ion exchange bed containing an ion exchange resin, which removes divalent cations from the process stream. The process stream then flows through a flash separator and a distillation column to reclaim MEG. The spent solid adsorbent material may be regenerated, without removing it from the hydrocarbon removal bed, using hot MEG, steam, or water that is produced during the MEG reclamation process. Similarly, the ion exchange resin may be regenerated in place using sodium chloride and distilled water that is produced during the MEG reclamation process.

A process for removing hydrocarbons and divalent cations from a rich MEG feed stream is also presented. The process includes the steps of providing a hydrocarbon removal bed containing a solid adsorbent material and passing the process stream through the hydrocarbon removal bed so that the hydrocarbons are adsorbed to the material. The process also includes the steps of divalent cation removal and MEG reclamation. A regeneration fluid, which may be water produced during the MEG reclamation process, is used to regenerate the spent solid adsorbent material without removing it from the hydrocarbon removal bed. Sodium chloride and water produced during the MEG reclamation process may be used to regenerate the spent ion exchange resin without removing it from the ion exchange bed.

Objects of this invention are to (1) provide a more efficient process to remove hydrocarbons and divalent cations from a rich MEG feed stream before it enters the reclamation process; (2) simplify the hydrocarbon and divalent cation removal processes; (3) reduce the volume, footprint, and cost of the processing equipment typically required to remove hydrocarbons and divalent cations from the rich MEG feed stream; (4) provide a renewable or reusable bed for hydrocarbon or divalent cation removal; and (5) facilitate the disposal of waste streams.

BRIEF DESCRIPTION OF THE DRAWINGS

The FIGURE presents an embodiment of a process for removing hydrocarbons and divalent cations from a rich MEG feed stream as part of a MEG reclamation process, practiced according to this invention.

ELEMENTS AND NUMBERING USED IN THE DRAWINGS AND THE DETAILED DESCRIPTION

10 Hydrocarbon and divalent cation removal process
15 Final production separator
20 Rich MEG feed stream
22 Hydrocarbon removal step
25 Hydrocarbon removal bed
30 Rich MEG feed stream with majority of hydrocarbons removed
35 Flash separator
40 Sodium chloride waste stream
45 Vaporized water and MEG stream
50 Distillation column
55 Lean MEG
60 Distilled water
65 Water storage tank
70 Heat exchanger
75 Heated distilled water stream
80 Combined distilled water and hydrocarbon stream
85 Ion exchange step
90 Ion exchange bed
95 Rich MEG feed stream with majority of hydrocarbons and divalent cations removed
100 Brine storage tank
105 Stream of sodium chloride brine solution
110 Waste stream of sodium chloride and calcium chloride brine

DETAILED DESCRIPTION OF THE PREFERRED EMBODIMENTS

In order to maximize the recovery of lean MEG, both hydrocarbons and divalent cations should be removed from the rich MEG feed stream before the MEG reclamation process begins. Because hydrocarbons in the feed stream may interfere with the ion exchange process by coating the ion exchange resin, the hydrocarbon removal step generally occurs before the ion exchange step.

As shown in the FIGURE, a preferred embodiment of a hydrocarbon and divalent cation removal process 10 practiced according to this invention begins with the final production separator 15, which produces a mixture of produced water and MEG commonly referred to as rich MEG. The rich MEG feed stream 20 is routed to a hydrocarbon removal step 22 comprised of dual hydrocarbon removal beds 25 which contain solid adsorbent material and alternate between adsorption and regeneration phases. Suitable adsorbent materials include, but are not limited to, DOWEX OPTIPORE® (Dow Chemical Co., Midland, Mich.). In the adsorption phase, hydrocarbons are selectively transferred from the rich MEG feed stream 20 to the surface of the solid adsorbent material. Although two hydrocarbon removal beds 25 are shown in the FIGURE, the step may use more than two beds or a single bed. The rich MEG feed stream with the majority of hydrocarbons removed 30 then exits the hydrocarbon removal beds 25 and flows to an ion exchange step 85.

A regenerable ion exchange resin may be used to adsorb the divalent cations from the rich MEG feed stream. In a preferred embodiment of the process, as shown in the FIGURE, the rich MEG feed stream with the majority of hydrocarbons removed 30 is routed to dual ion exchange beds 90 which contain a strong cation exchange resin in the sodium form. This resin removes divalent cations from the rich MEG feed stream by adsorbing the divalent cations and displacing the sodium cations. Although two ion exchange beds 90 are shown in the FIGURE, the ion exchange step may use more than two beds or a single bed.

The rich MEG feed stream with the majority of hydrocarbons and divalent cations removed 95 then exits the ion exchange beds 90 and flows to the MEG reclamation process. The MEG reclamation process begins in a flash separator 35, where the pressure is reduced in order to separate salts from the rich MEG and water. A sodium chloride waste stream 40 exits the bottom end of the flash separator 35, while the vaporized water and MEG stream 45 exits the top end and flows to the distillation column 50. The distillation column 50 uses partial condensation to separate the water and MEG components of the vaporized water and MEG stream 45. Lean MEG 55 exits the bottom end of the distillation column 50 and distilled water 60 is discharged from the top end of the distillation column 50. The distilled water 60 may be treated as waste or recycled to the regeneration process for the hydrocarbon removal beds 25 or the ion exchange beds 90.

Regeneration of the hydrocarbon removal beds may be accomplished with steam, hot MEG, or hot water. In the embodiment shown in the FIGURE, distilled water 60 from the distillation column 50 is sent to a water storage tank 65. At the beginning of the regeneration process, one of the hydrocarbon removal beds 25 is taken off-line by diverting the flow of the rich MEG feed stream 20 to the alternate bed 25. Distilled water 60 from the water storage tank 65 is then heated by a heat exchanger 70 to generate steam in the range of 100 to 200 pounds per square inch (psi). The heated distilled water stream 75 is routed through the off-line hydrocarbon removal bed 25 in a direction opposite that of the flow of the rich MEG feed stream 20. Hydrocarbons that have been adsorbed to the solid adsorbent material inside the hydrocarbon removal bed 25 are transferred to the heated distilled water stream 75, and the combined distilled water and hydrocarbon stream 80 exits from the top of the hydrocarbon removal bed 25. The combined distilled water and hydrocarbon stream 80 is then recycled back into the final production separator 15.

Regeneration of the ion exchange beds may be accomplished with water containing large amounts of a salt such as sodium chloride. In the embodiment shown in the FIGURE, the sodium chloride waste stream 40 from the flash separator 35 is combined with distilled water 60 from the distillation column 50 in a brine storage tank 100 to form a sodium chloride brine solution known as regeneration brine. At the beginning of the regeneration process, one of the ion exchange beds 90 is taken off-line by diverting the flow of the rich MEG feed stream with the majority of hydrocarbons removed 30 from that bed 90 to the alternate bed 90. A stream of sodium chloride brine solution 105 from the brine storage tank 100 is then routed through the off-line ion exchange bed 90 in a direction opposite that of the flow of the rich MEG feed stream with the majority of hydrocarbons removed 30. Cations that have been adsorbed to the ion exchange resins inside the ion exchange bed 90 leave the resins and enter the stream of sodium chloride brine solution 105, forming a waste stream of sodium chloride and calcium chloride brine 110. This waste stream 110 may be handled as waste or recycled back to the brine storage tank 100 and re-used to regenerate the ion exchange beds 90 until the concentration of ions increases to a level that impairs regeneration of the resin.

While preferred embodiments of a system and process for removing hydrocarbons and divalent cations from rich MEG feed streams have been described in detail, a person of ordinary skill in the art understands that certain changes can be made in the arrangement of process steps and type of components used in the system and process without departing from the scope of the following claims.

What is claimed is:

1. A process for removing hydrocarbons and divalent cations from a rich MEG feed stream, the process comprising the steps of:
    (i) passing the rich MEG feed stream through a hydrocarbon removal bed where the hydrocarbons are adsorbed by a solid adsorbent material;
    (ii) passing the rich MEG feed stream from the hydrocarbon removal bed through an ion exchange bed where the divalent cations are adsorbed by an ion exchange resin; and
    (iii) passing the rich MEG feed stream from the ion exchange bed through a flash separator followed by a distillation column.

2. A process according to claim 1 further comprising the step wherein a regeneration fluid is used to regenerate the solid adsorbent material without removing it from the hydrocarbon removal bed.

3. A process according to claim 2 wherein the regeneration fluid is water that is produced as the rich MEG feed stream is treated in the distillation column.

4. A process according to claim 2 wherein the regeneration fluid is routed to a final production separator after it flows through the hydrocarbon removal bed.

5. A process according to claim 1 further comprising the step wherein a brine solution is used to regenerate the ion exchange resin without removing it from the ion exchange bed.

6. A process according to claim 5 wherein the brine solution is comprised of sodium chloride that is produced as the rich MEG feed stream is treated in the flash separator and water that is produced as the rich MEG feed stream is treated in the distillation column.

7. A process for removing divalent cations from a rich MEG feed stream, the process comprising the steps of:
    (i) passing the rich MEG feed stream through an ion exchange bed where the divalent cations are adsorbed by an ion exchange resin; and
    (ii) passing the rich MEG feed stream from the ion exchange bed through a flash separator followed by a distillation column.

\* \* \* \* \*